United States Patent
Black et al.

(10) Patent No.: US 8,961,174 B2
(45) Date of Patent: Feb. 24, 2015

(54) SYSTEM FOR PRODUCING COMBINED BURSTS OF AIR AND WATER FOR CLEANING TEETH

(75) Inventors: Craig Kortick Black, Eindhoven (NL); Dainia Edwards, Eindhoven (NL); Skookumchuck Pong, Eindhoven (NL); Jonathan Kling, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 13 days.

(21) Appl. No.: 13/819,813

(22) PCT Filed: Sep. 22, 2011

(86) PCT No.: PCT/IB2011/054167
§ 371 (c)(1),
(2), (4) Date: Feb. 28, 2013

(87) PCT Pub. No.: WO2012/042445
PCT Pub. Date: Apr. 5, 2012

(65) Prior Publication Data
US 2013/0177869 A1    Jul. 11, 2013

Related U.S. Application Data

(60) Provisional application No. 61/387,527, filed on Sep. 29, 2010, provisional application No. 61/447,382, filed on Feb. 28, 2011.

(51) Int. Cl.
*A61C 17/028* (2006.01)
*A61C 17/16* (2006.01)
*A61C 1/00* (2006.01)

(52) U.S. Cl.
CPC ............... *A61C 17/16* (2013.01); *A61C 17/028* (2013.01); *A61C 1/0092* (2013.01)

USPC .............................. 433/88; 433/89; 601/162

(58) Field of Classification Search
USPC ................ 433/80–89; 601/160–165; 604/33; 239/104, 106, 407, 413, 418, 433
See application file for complete search history.

(56) References Cited

U.S. PATENT DOCUMENTS

| 8,753,117 | B2 * | 6/2014 | Edwards et al. ................. 433/88 |
| 2003/0013063 | A1 | 1/2003 | Goldman |
| 2003/0204154 | A1 | 10/2003 | Chen et al. |
| 2010/0167236 | A1 * | 7/2010 | Edwards et al. ................. 433/89 |

FOREIGN PATENT DOCUMENTS

WO        03039392 A1     5/2003
WO    WO 2010076694 A1 *  7/2010

* cited by examiner

*Primary Examiner* — Edward Moran

(57) ABSTRACT

The apparatus includes a motor (20) which drives a first compound gear (28) having first and second portions (26, 32), the second portion driving a second compound gear (36). The second compound gear has one portion (38) which has teeth over only one half the circumference thereof. The apparatus further includes an air cylinder (12) and a rack (62) and a spring assembly (66) a sealing end portion (64) of the rack fitting in a fluid-tight relationship with the air cylinder, wherein the rack member is engaged by the one portion of the second compound gear, compressing the spring when the teeth thereon engage the rack member. When the no-teeth portion comes adjacent the rack member, the rack is released and the sealing end of the rack member is forced by action of the spring into the air cylinder, producing bursts of air. The second compound gear also drives a peristaltic pump, producing liquid in bursts which are directed to a mixing chamber 58, from which a stream of liquid droplets exit through exit 16.

11 Claims, 3 Drawing Sheets

SYSTEM FOR PRODUCING COMBINED BURSTS OF AIR AND WATER FOR CLEANING TEETH

This invention relates generally to apparatus for cleaning teeth using a combination of bursts of air and bursts of fluid to produce a desired air/fluid mix, and more particularly concerns a single assembly for producing both air bursts and fluid bursts in coordination.

In systems which produce teeth cleaning with a combination of bursts of air and fluid, such as water, it is important that the air and fluid are mixed in a way to deliver the greatest efficacy of cleaning. In addition it is important to coordinate the timing of these two functions while still being relatively simple in structure and operation, and sufficiently small to fit within a specific device footprint. Use of separate liquid and air delivery systems typically have some problems with timing, as well as space constraints and the need for dual power sources. It would be advantageous to have an appliance in which a single power source can be used to accomplish both the liquid and air generating functions and provide coordinated timing thereof.

An apparatus for use in a liquid droplet system for cleaning teeth for producing both successive bursts of air and successive bursts of liquid with one force assembly, comprising: a single motor, a first gear assembly driven by the single motor; a second gear assembly, wherein one portion of the first gear assembly drives the second gear assembly; a liquid pump driven by the second gear assembly to produce successive bursts of liquid as the motor operates; and a spring driven assembly for producing bursts of air; wherein the second gear assembly includes a portion which drives the spring assembly, such that each revolution of the motor produces a burst of air and a burst of liquid, which then are mixed together to form a stream of high speed droplets for cleaning teeth.

FIGS. 1-5 show an apparatus, generally at 10, for producing successive bursts of air and liquid, such as water, which mix to produce a stream of air and fluid droplets used for cleaning teeth, especially the interproximal areas of the teeth. Apparatus 10 forms the major part of a complete teeth-cleaning appliance, which includes a cover, a power source and control elements for operating the apparatus. Those elements are conventional in a liquid droplet type cleaning apparatus, and hence not specifically shown nor described in detail herein.

Figure 1:
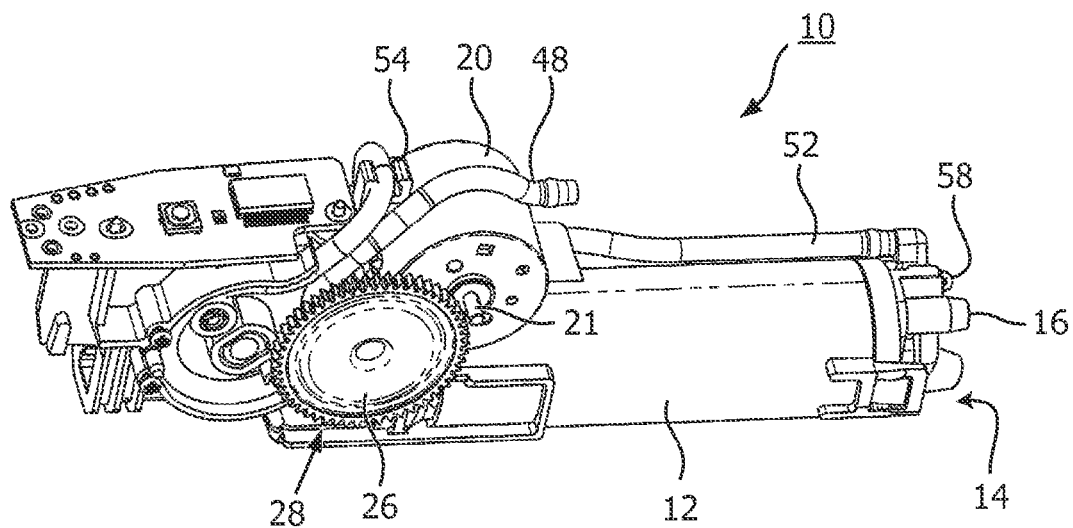
FIG. 1 is a perspective view showing the apparatus.
Figure 2:
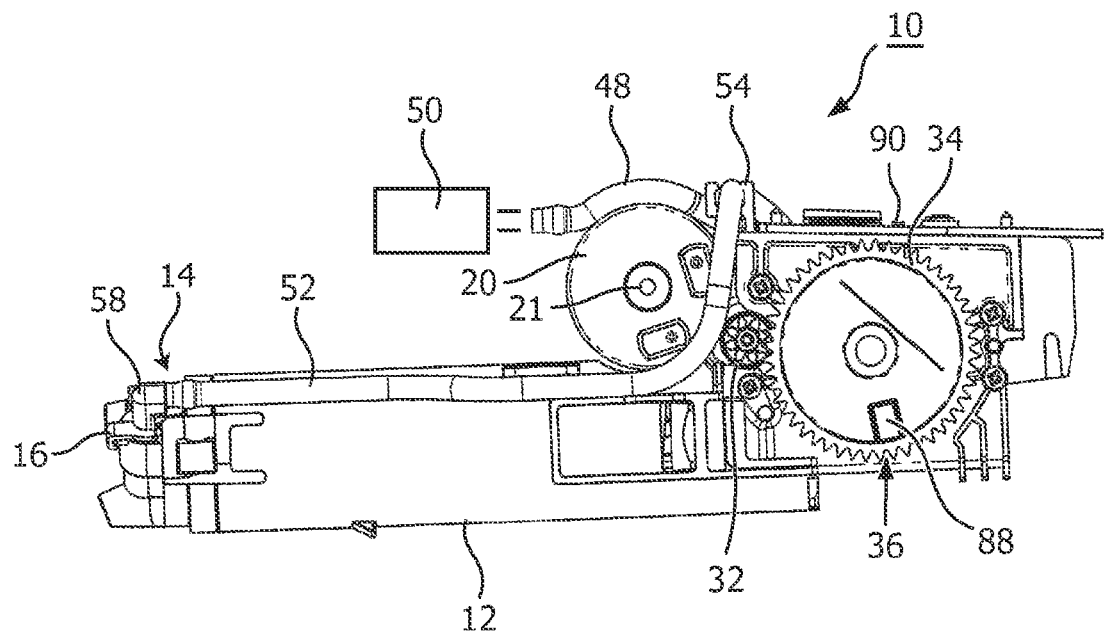
FIG. 2 is an elevational view of the opposing side of the apparatus of FIG. 1.

Referring now specifically to FIGS. 1 and 2, apparatus 10 includes an air cylinder 12, which in the embodiment shown is approximately 2.5 inches long with an internal diameter of 0.5-1.0 inches. At a distal end 14 of air cylinder 12 is a nozzle 16 through which a mix of water or other liquid bursts and fluid, typically air, exit, in the form of a stream of high velocity liquid droplets. The liquid droplets are directed toward the teeth of a user, particularly the interproximal area, for cleaning.

Figure 3:
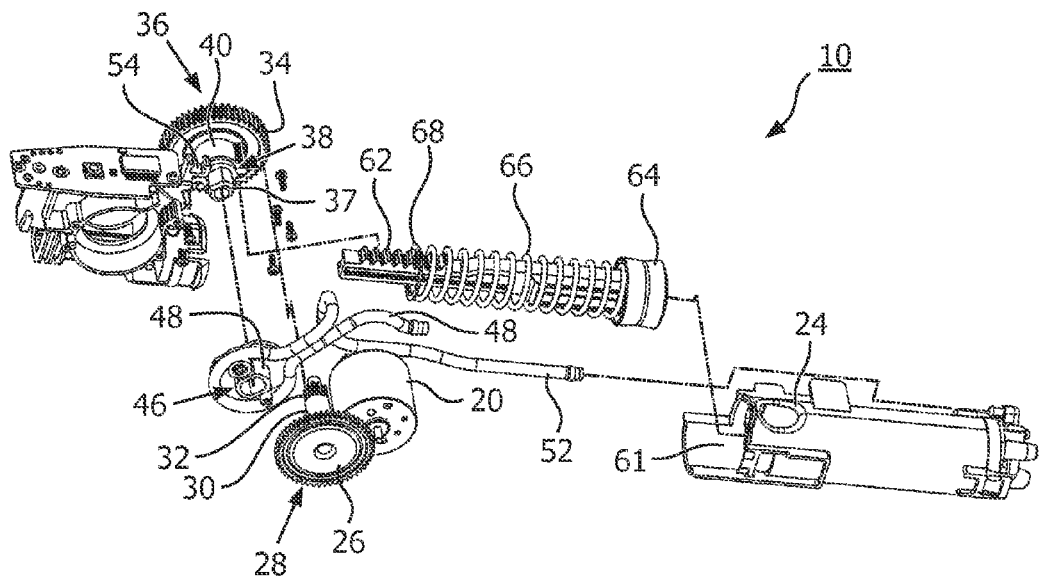
FIG. 3 is an exploded view of the apparatus of FIG. 1.
Figure 4:
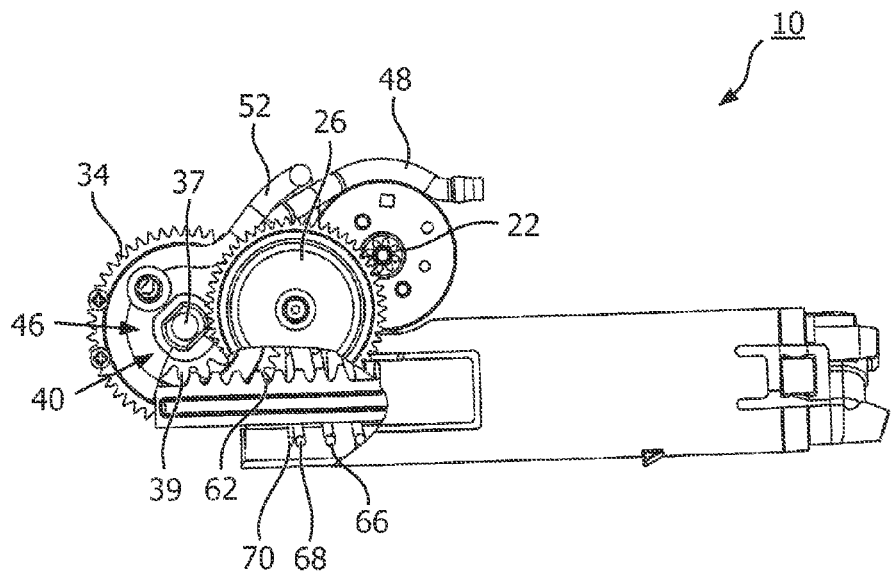
FIG. 4 is a partially cutaway elevational view of FIG. 1.
Figure 5:
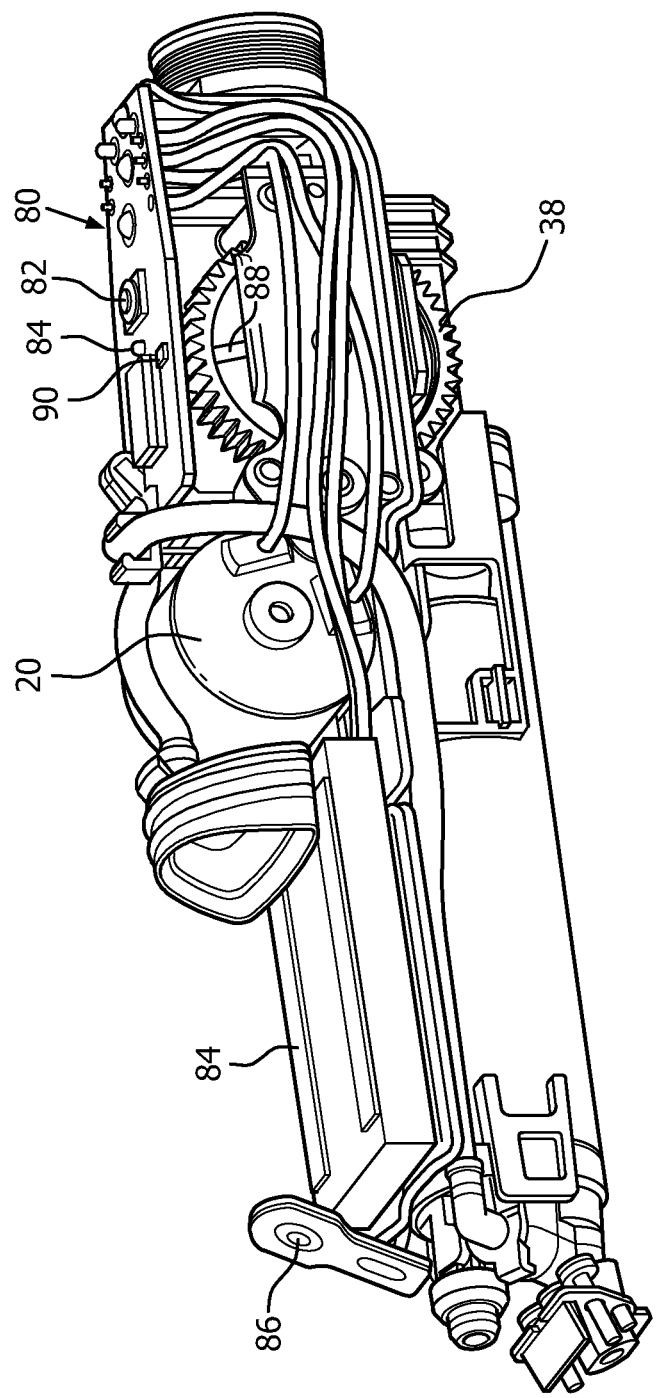
FIG. 5 is another perspective view showing the appratus.

The apparatus includes a motor 20 which in the embodiment shown is a DC motor, typically with high torque, e.g. 15 Newton meters, although this value is typically achieved after gear reduction. The motor itself thus does not have to produce such a value of torque itself. Such motors are widely commercially available. Various motors are suitable. Motors made by Mitsumi are for instance examples of a suitable motor. Motor 20 includes an output shaft 21 on which is mounted a motor drive gear 22 (FIG. 4). In the embodiment shown, there are 8 teeth on the motor drive gear. The number of teeth on gear 22, as with the number of teeth on the other gears, can be varied. Motor 20 is positioned at 24 at the rear upper surface of air cylinder 12. Motor drive gear 22 engages a first (outer) gear part 26 of a first compound gear 28 located at a first side of the apparatus. The first compound gear 28 in the embodiment shown is made of plastic as are the other gears, however it could be made of other material as well. The first gear part 26 of gear 28 in the embodiment shown has 53 teeth. The motor drive gear 22 in operation rotates it in a clockwise direction. The first compound gear 28 also includes a gear shaft 30 and a second (inner) gear part 32 coincident with the distal end of shaft 30, as shown in FIG. 3. In the embodiment shown, the second gear part of the first compound gear has 8 teeth.

The shaft 30 with the second gear part 32 of the first compound gear 28 extends through apparatus 10 and mates with a first (outer) gear part 34 of a second compound gear 36 positioned on an opposing side of the apparatus. In the embodiment shown, the first gear part 34 of the second compound gear has 48 teeth, although this can be varied, as noted above. A second (inner) gear part 38 of second compound gear 36 is positioned adjacent the first gear part 34 on a center gear shaft 37. The second gear part of the second compound gear has two parts, a first part comprising a partial set of 8 teeth referred to at 39 spaced around approximately one half of the circumference of the second gear part and a second part 40 which has no teeth, i.e. the surface is smooth at the base of the teeth portion of the second gear part. Typically, but not necessarily, the two parts are each one-half of the second gear part.

The second compound central gear shaft 37 extends back through the apparatus to the first side of the apparatus and engages a peristaltic fluid pump assembly 46, which includes a pump 48. Peristaltic pump assembly 46 includes a first tube section 48 which extends to a fluid reservoir 50. In the embodiment shown, the fluid in reservoir 50 is water, although other fluids can be used as well. These include various formulations which assist in cleaning teeth, such as chlorhexidine, hydrogen peroxide based rinses, mixtures of water, baking soda, essential oils or mouthwash, for example. The peristaltic pump assembly 46 also includes a second tube 52 which extends from the pump and above the body of the apparatus, in a U-shaped mounting element 54 and then along the outer surface of the air cylinder to a mixing chamber 58 on the distal end of the air cylinder.

The second gear part 38 of the second compound gear 36 mates with a linear rack member 62 which is positioned at a proximal end 61 of air cylinder 12. In the embodiment shown, rack member 62 is approximately 2 inches long and includes a set of 8 spaced teeth on the upper surface thereof. The distal end of rack member 62 includes a seal member 64 which mates in a fluid tight relationship with the interior surface of air cylinder 12. Extending from the distal end of rack 62 at seal 64 and encircling the rack along most of the length thereon is a compression spring 66. The proximal end 68 of spring 66 is positioned against a stop element 70 in body portion 20, as shown in FIG. 4.

In operation, as motor drive gear 22 turns, rack 62 moves rearwardly by action of the partial set of teeth 39 of the second gear part of the second compound gear, away from the proximal end 61 of the air cylinder, compressing spring 66 against stop 70. Air enters the air cylinder through an opening at distal end 14. In the embodiment shown, spring 66 undergoes 30 mm of compression. In the embodiment, the spring is compressed successively every 400 to 900 milliseconds depending on the precise rpm of the motor. It is possible to go faster than every 400 ms, even down to 100 ms. When the second compound gear 36 rotates so that the non tooth gear portion 40 of the second gear part of compound gear 38 comes adjacent the rack, such that there is no gear connection between the second compound gear and the rack, with no gear contact holding the rack in position, spring 66 operates to move the rack quickly forwardly, moving the sealed end of the rack forwardly in the air cylinder, forcing a burst of air into the mixing chamber, along with liquid (water) burst, produced by action of the pump, driven by the shaft of the second compound gear. Typically, there is one shot of air per revolution of the motor shaft, every 400-900 milliseconds (or faster) further; there is approximately 0.15 mm of fluid provided to the mixing chamber per revolution of the motor shaft.

The successive bursts of air and liquid are brought together in the mixing chamber 58, with proper, consistent timing, from which the resulting mixture exits through nozzle 16, directed toward the teeth of the user for cleaning thereof.

Accordingly, a single motor apparatus has been disclosed which is arranged to provide the necessary motor force for both the generation of fluid bursts of bursts of air to produce a stream of liquid droplets.

Although a preferred embodiment has been disclosed for purposes of illustration, it should be understood that various changes and modifications and substitutions could be made in the preferred embodiment without departing from the spirit of the invention as defined by the claims which follow:

1. An apparatus for use in a liquid droplet system for cleaning teeth for producing successive bursts of air and successive bursts of liquid with one motor assembly, comprising:
   a single motor having an output shaft;
   a motor drive gear attached to the motor output shaft
   a first compound gear having a first gear portion and a second gear portion;
   a second compound gear having a first gear portion and a second gear portion, the second gear portion having a first part with teeth spaced around a circumference thereof and a remainder of the second gear portion having no teeth around the circumference thereof, wherein the motor drive gear drives the first gear portion of the first compound gear and wherein the second gear portion of the first compound gear drives the first gear portion of the second compound gear;
   an air cylinder;
   a mixing chamber at a distal end of the air cylinder, the mixing chamber having an exit nozzle for a mix of liquid and air;
   a rack member having a distal sealing end which mates with an interior surface of the air cylinder in a fluid-tight relationship, wherein the second gear portion of the second compound gear mates with and drives the rack;
   a spring member mounted such that as the rack is moved by action of the second gear portion of the second compound gear the spring compresses; and
   a liquid pump connected to the second compound gear such that as the second compound gear turns, successive bursts of liquid are directed into the mixing chamber, and wherein when the remainder of the second gear portion having no teeth around the circumference thereof comes adjacent to the rack, such that there is no connection between the second compound gear and the rack, the spring moves the rack within the air cylinder at such a rate to produce bursts of air to the mixing chamber such that a resulting mix stream of droplets exit at high velocity through the nozzle for cleaning of the teeth.

2. The apparatus of claim 1, wherein the first gear portion of the first compound gear, driven by the motor drive gear has a substantially greater number of teeth than the second gear portion of the first compound gear.

3. The apparatus of claim 2, wherein the first gear portion of the first compound gear has at least five times as many teeth as the second gear portion of the first compound gear and wherein the motor drive gear has approximately the same number of teeth as the second gear portion of the first compound gear.

4. The apparatus of claim 1, wherein the first gear portion of the second compound gear has a substantially greater number of teeth than the second gear portion of the second compound gear, wherein the second gear portion has teeth over only a part of the second gear portion, wherein when the remainder of the second gear portion, without teeth, of the second compound gear comes adjacent the rack, the rack is released and moves quickly through the air cylinder by spring action.

5. The apparatus of claim 3, wherein the first gear portions of the first and second compound gears are positioned on opposite sides of the apparatus.

6. The apparatus of claim 1, wherein the fluid pump is a peristaltic pump.

7. The apparatus of claim 1, wherein the spring compresses approximately 30 mm during operation, wherein the pump produces liquid bursts of approximately 0.15 ml per revolution of the motor and wherein air bursts are produced every 400-900 milliseconds, timed to produce a mixing effect in the mixing chamber.

8. The apparatus of claim 7, wherein the air bursts are produced every 400-900 milliseconds.

9. The apparatus of claim 1, wherein the liquid is water.

10. The apparatus of claim 1, including an apparatus body, which includes a stop member (70) against which the spring member is compressed and wherein the distal end of the spring member is connected to the sealing end of the rack member, such that when the rack member is released, the spring action forces the sealing end of the rack member along the length of the air cylinder toward a distal end thereof.

11. An apparatus for use in a liquid droplet system for cleaning teeth for producing both successive bursts of air and successive bursts of liquid with one motor assembly, comprising:
   a single motor,
   a first gear assembly driven by the single motor;
   a second gear assembly, wherein one portion of the first gear assembly drives a first gear portion of the second gear assembly;
   a liquid pump driven by the second gear assembly to produce successive bursts of liquid as the motor operates; and
   a spring driven assembly for producing bursts of air that includes an air cylinder a spring member, and a linear rack including a sealing member at one end thereof which mates with an interior surface of the air cylinder in a fluid-tight relationship, wherein a second gear portion of the second gear assembly has a first part with teeth spaced around a circumference thereof and a remainder of the second gear portion having no teeth around the circumference thereof, the second gear portion of the second gear assembly configured to move the linear rack when the part having teeth engage with the linear rack to compress the spring member and to release the spring member when the remainder of the second gear portion having no teeth comes adjacent to the linear rack, such that there is no connection between the second gear assembly and the linear rack, to produce a burst of air from the spring-driven assembly for each revolution of the single motor, such that each revolution of the single motor produces a coordinated burst of air and burst of liquid, which then mix together to form a stream of high speed droplets for cleaning teeth.

\* \* \* \* \*